United States Patent [19]

Lippsmeier et al.

[11] 4,020,110
[45] Apr. 26, 1977

[54] PRODUCTION OF TERTIARY METHYLPHOSPHINE OXIDES

[75] Inventors: Bernd Lippsmeier, Huth-Knapsack; Klaus Hestermann, Erftstadt Bliesheim; Martin Reuter, Frankfurt am Main-Unterliederbach, all of Germany

[73] Assignee: Hoechst Aktiengesellschaft, Frankfurt am Main, Germany

[22] Filed: Mar. 20, 1975

[21] Appl. No.: 560,294

[30] Foreign Application Priority Data

Mar. 22, 1974 Germany ............... 2413823

[52] U.S. Cl. .................... 260/606.5 P
[51] Int. Cl.² .................... C07F 9/53
[58] Field of Search ............ 260/606.5 P

[56] References Cited

UNITED STATES PATENTS

| | | | |
|---|---|---|---|
| 3,030,421 | 4/1962 | Reuter et al. | 260/606.5 P |
| 3,660,495 | 5/1972 | Lin | 260/606.5 P |
| 3,732,316 | 5/1973 | Lin | 260/606.5 P |
| 3,928,463 | 12/1975 | Reuter | 260/606.5 P |

OTHER PUBLICATIONS

Chemical Abstracts, 68, 87350q, (1968).
Chemical Abstracts, 70, 115227s, (1969).
Hellmann et al., Ann., vol. 659, pp. 49–63, (1962).
Epstein et al., Tetrahedron, vol. 18, pp. 1211–1219, 1231–1242, (1962).
Trippett, J. Chem. Soc., pp. 2813–2816, (1961).
Buckler, J. A. C. S., vol. 82, pp. 4215–4220, (1960).
Buckler et al., J. A. C. S., vol. 82, pp. 2076–2077, (1960).

Primary Examiner—Helen M. S. Sneed
Attorney, Agent, or Firm—Connolly and Hutz

[57] ABSTRACT

Production of tertiary methylphosphine oxides of the general formula

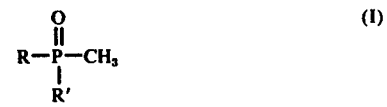

in which R and R' each stand for identical or different, branched or unbranched, substituted or unsubstituted alkyl, cycloalkyl, aralkyl or aryl groups having from 1 to 18 carbon atoms. The compounds are produced by subjecting tertiary hydroxymethylphosphines of the general formula

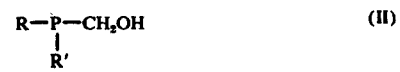

in which R and R' have the meanings given above, to a thermal rearrangement reaction at temperatures higher than about 90° C or, in the presence of a catalyst, at temperatures within the range −10 and +250° C.

4 Claims, No Drawings

PRODUCTION OF TERTIARY METHYLPHOSPHINE OXIDES

The present invention relates to a process for making tertiary methylphosphine oxides of the general formula:

$$R-\underset{\underset{R'}{|}}{\overset{\overset{O}{\|}}{P}}-CH_3 \quad (I)$$

in which R and R' each stand for identical or different, branched or unbranched, substituted or unsubstituted alkyl, cycloalkyl, aralkyl or aryl groups other than hydroxymethyl groups, having from 1 to 18, preferably from 1 to 6, more preferably from 1 to 2, carbon atoms, the substituents of those groups being inert under the reaction conditions.

The process of the present invention is more particularly used for making trimethylphosphine oxide.

It is known that tertiary phosphine oxides can be made by a plurality of processes (Houben-Weyl, Methoden der organischen Chemie, Georg Thieme Verlag, Stuttgart, volume XII/1, pages 135 et seq. (1963). As compared therewith, there are only a few processes which can be used for making tertiary methylphosphine oxides under attractive conditions. Methyldiphenylphosphine oxides can be made, for example by reacting diphenyl-orthophosphinic acid triiodide with methyl iodide and hydrolyzing the product so obtained (H. Hoffmann, R. Grunwald and L. Horner, Chem. Ber. 93, 861 (1960); L. Anschutz, H. Kraft and K. Schmidt, Liebigs Annalen 542, 14 (1939)).

A further generally applicable method comprises subjecting phosphonium compounds containing methyl groups to a splitting reaction with silver oxide or aqueous alkalies. (Houben-Weyl, Methoden der organischen Chemie, Georg Thieme Verlag, Stuttgart, volume XII/1, page 144 (1963)).

It is also possible to produce tertiary methylphosphine oxides with the aid of organo-metal compounds, such as Grignard reagents, by reacting them with phosphorus halides, such as PCl$_5$, POCl$_3$ or orthophosphoric acid tetrachlorides. Trimethylphosphine oxide can be obtained, for example, in yields of 52% by subjecting phosphorus oxychloride to a Grignard reaction with methylmagnesium chloride (A. B. Burg and W. E. McKee, J. Amer. Chem/. Soc. 73, 4590 (1951); J. Goubeau and W. Berger, Z. anorg. Chemie 304, 147 (1960)).

All those processes are, however, not fully satisfactory in producing moderate yields, in using starting materials which are not readily available, and in necessitating considerable expenditure of work and chemicals. This is the reason why they did not gain practical interest.

The present invention now unexpectedly provides a process for making tertiary methylphosphine oxides by transforming a =P—CH$_2$OH— group into a $$=\overset{\overset{O}{\|}}{P}-CH_3$$

grouping without any need to use chemicals which are difficult to handle and costly, e.g. methylmagnesium chloride or methyl iodide. The starting materials used in the above reaction are inexpensive and readily obtainable by reacting a suitable trivalent phosphorus compound containing P—H— bonds, such as secondary phosphines, with formaldehyde.

The present invention relates more particularly to a process for making tertiary methylphosphine oxides of the general formula:

$$R-\underset{\underset{R'}{|}}{\overset{\overset{O}{\|}}{P}}-CH_3 \quad (I)$$

in which R and R' each stand for identical or different, branched or unbranched, substituted or unsubstituted alkyl, cycloalkyl, aralkyl or aryl groups, other than hydroxymethyl groups, having from 1 to 18, preferably from 1 to 6, more preferably from 1 to 2, carbon atoms, the substituents of those groups being inert under the reaction conditions, which process comprises subjecting tertiary hydroxymethylphosphines of the general formula:

$$R-\underset{\underset{R'}{|}}{P}-CH_2OH \quad (II)$$

in which R and R' have the meanings given above, to a thermal rearrangement reaction at temperatures higher than about 90° C or in the presence of a catalyst at temperatures within the range −10° C and +250° C.

It is possible for the above rearrangement reaction to be effected in the presence of inert, e.g. polar organic solvents or dispersants, such as alcohols, glycols, formamides, aliphatic or aromatic nitriles, ethers, halogenated aliphatic or aromatic hydrocarbons, alkylated urea derivatives, cyclic or linear sulfones, carboxylic acid esters, anhydrides or amides, sulfoxides or blends thereof. The rearrangement reaction should more preferably be effected in the presence of dimethylformamide, benzonitrile, propionitrile, dioxane, o-dichlorobenzene, sulfolane, N-methylpyrrolidone, dimethylsulfoxide or methylphosphine oxide of general formula (I), the latter being prefabricated in each particular case.

It is even more preferable for the rearrangement reaction to be carried out in the presence of unpolar solvents or dispersants. In this latter case, it is particularly advantageous to use unbranched or branched aliphatic or cycloaliphatic or aromatic hydrocarbons, such as petroleum ether, octane, dodecane or decaline.

The thermal treatment should conveniently be effected at temperatures within the range 90° and 180° C. In those cases in which the rearrangement is effected in the presence of catalysts, it is good practice to use a Lewis acid catalyst, e.g. BF$_3$.etherate. The catalyst should preferably be used in a proportion of at least 1 weight %. If carried out in the presence of catalysts it is most preferable for the rearrangement reaction to be carried out at temperatures within the range −10° and +180° C.

It is also possible for the rearrangement reaction to be carried out in the absence of solvents or dispersants. In this case, it is advantageous for it to be effected in a thin layer evaporator, tubular reactor or packed column, especially in a column packed with metal powder, quartz sand, glass rings or balls, at temperatures within the range 130° and 250° C.

The use of an unpolar solvent or dispersant has the technically beneficial effect that the resulting reaction product does generally not mix with the diluent used in each particular case and that the desirable phosphine oxide is easy to separate by phase separation. In some cases, it is possible for dissolved contaminants or by-products to be retained in the second phase, which means an additional purification effect.

If the hydroxymethylphosphines used have a sufficient thermal stability, it is possible for the solvent to be completely omitted in carrying out the rearrangement reaction which, however, should then be effected within periods as short as possible.

A particularly preferred embodiment of the present process comprises making tertiary methylphosphine oxides from secondary phosphine. To this end, the secondary phosphine is reacted at atmospheric pressure at temperatures lower than 40° C, preferably within the range 30° and 35° C, with formaldehyde, paraformaldehyde or trioxane in the presence of polar organic solvents being inert with respect to the reactants and the resulting reaction product, the resulting tertiary hydroxymethylphosphine is left unseparated and subjected to a thermal rearrangement reaction at temperatures higher than about 90° C, preferably within the range 90° and 250° C, more preferably within the range 90° and 180° C, or admixed with a catalyst and then treated at temperatures within the range −10° and +250° C.

The polar solvents used in the embodiment just described should conveniently be selected from alcohols, glycols, formamides, aliphatic or aromatic nitriles, ethers, halogenated aliphatic or aromatic hydrocarbons, alkylated urea derivatives, cyclic or linear sulfones, carboxylic acid esters, anhydrides or amides, sulfoxides or blends thereof. Particularly useful are dimethylformamide, benzonitrile, propionitrile, dioxane, o-dichlorobenzene, sulfolane, N-methylpyrrolidone or dimethylsulfoxide, especially in admixture with lower alcohols, such as methanol and ethanol. If the rearrangement reaction is effected in the presence of catalysts, it is good practice for the catalysts to be selected from carbon tetrachloride or tetrabromide or Lewis acids, e.g. $BF_3$.etherate. The catalysts should preferably be used in proportions of at least 1 weight % and the rearrangement reaction should be effected at temperatures within the range −10° and +180° C.

The reaction periods are within the range about 2 and 60 hours.

It is also advantageous for the reaction to be carried out under inert gas, e.g. nitrogen, carbon dioxide or argon.

Tertiary phosphine oxides are used in the dyeing industries, e.g. as agents improving the absorptive power and fastness to light, in detergents, for the extractive separation of rare earths and in the catalytic decontamination of off-gases, e.g. for the removal of sulfur compounds from gas mixtures.

EXAMPLE 1

46 g (0.5 mol) of (hydroxymethyl)-dimethylphosphine was added dropwise with thorough agitation, within 30 minutes at 130° C and under nitrogen to 150 ml of benzonitrile, in a 250 ml round flask, and the whole was heated for a further 8 hours to 130° C. After the reaction, the solvent was distilled off at 70° C under a pressure of 0.2 mm Hg. 45.8 g of a slightly yellowish and highly viscous oil, which crystallized gradually on cooling, was obtained. The crude product was subjected to NMR-spectroscopy and gas chromatography and found to contain 77.8% of trimethylphosphine oxide. ($^{31}P$—NMR: —36.2 ppm). Titration with iodine in an acid medium indicated that the crude product was practically free from trivalent phosphorus compounds.

The product could be further purified by sublimation under vacuum. Trimethylphosphine oxide melting at 138.5° – 140° C was obtained in a yield of 34.5 g (75% of the theoretical). In its chemical, physical and spectroscopic properties, the product so made was found to be identical with a comparative product prepared from methylmagnesium chloride and phosphorus oxychloride (Houben-Weyl, Methoden der organischen Chemie, vol. XII/1, pages 158 – 159 (1963)).

EXAMPLES 2, 3, and 4

The procedure was the same as that described in Example 1 save that the benzonitrile was replaced once by dimethylsulfoxide once by N-methylpyrrolidone and once by dimethylformamide. Results similar to those in Example 1 were obtained at the boiling temperature of these solvents. The reaction periods were within the range 4 and 8 hours.

EXAMPLE 5

30 g of benzonitrile was admixed dropwise with very careful exclusion of oxygen (argon atmosphere), with thorough agitation, at 130° C and within 20 minutes, with a mixture of 30 g of benzonitrile and 30 g of (hydroxymethyl)-dicyclohexylphosphine. Following this, the whole was thoroughly stirred for altogether another 10 hours at 130° C. The solvent was removed under vacuum (70° C at 1–2 mm Hg) and 29.4 g of a slightly yellowish, highly viscous oil which crystallized gradually on standing, was obtained. Titration with iodine and NMR-spectroscopy indicated that the crude product contained 78.4% of methyl-dicyclohexylphosphine oxide. The product was further purified by fractional distillation under vacuum. 21.1 g of a colorless crystalline product melting at 87° – 90° C was obtained at 151° – 152° C under 0.3 mm Hg. Elementary analysis and NMR-spectroscopy indicated that 97 – 98% was methyl-dicyclohexylphosphine oxide ($^{31}P$—NMR: – 55 ppm). The yield was 70.3% of the theoretical.

EXAMPLE 6

100 g of o-dichlorobenzene was heated to 180° C under nitrogen. 46 g (0.5 mol) of (hydroxymethyl)-dimethylphosphine was added dropwise within 15 minutes thorough agitation. Following this, the whole was stirred for a further 6 hours at 180° C under reflux. After cooling, there were obtained two phases which were separated from each other in known manner, in a funnel separator. The upper phase contained trimethylphosphine oxide as desirable rearrangement product. The product was treated under vacuum to remove solvent residues, if any. 44.6 g of a slightly yellowish viscous oil which crystallized on cooling (mp: 125° – 135° C) was obtained. The product was identical with that obtained in Example 1. It contained 74.6% of trimethylphosphine oxide. A further minor quantity of final product was in the solvent phase and recovered therefrom after removal of the solvent. The crude product can be further purified by subjecting it to the treatment described in Example 1.

The same result as that described hereinabove was obtained by replacing the o-dichlorobenzene by octane, decaline or toluene. The compounds were used at their respective boiling temperature. The reaction periods were within the range 8 and 20 hours and the yields were within the range 76 and 80% of the theoretical.

EXAMPLE 7

46 g (0.5 mol) of (hydroxymethyl)-dimethylphosphine was so supplied under nitrogen at 240° C to a thin layer evaporator that the total reaction period was 6 hours. 43 g of a slightly brownish product which solidified gradually on cooling was obtained. NMR-spectroscopy and iodometric titration indicated a 87.5% rearrangement of the phosphine used. The crude product was subjected to sublimation under vacuum and colorless crystalline trimethylphosphine oxide melting at 135° – 138° C was obtained.

EXAMPLE 8

100 ml of benzonitrile containing 2.5 weight % of $BF_3$.etherate was added dropwise, within 2 hours, at 125° C, under nitrogen and with thorough agitation to a solution of 46 g (0.5 mol) of (hydroxymethyl)-dimethylphosphine in 100 ml of benzonitrile. Following this the whole was heated for a further 1–1 hours to reflux temperature and the solvent was removed by distillation under vacuum. The residue was a slightly yellowish viscous oil which solidified gradually on cooling. 74.2% of the crude product was trimethylphosphine oxide. The product was purified by sublimation under vacuum and found to be identical with that obtained in Example 1.

EXAMPLE 9

30 g (1 mol) of paraformaldehyde was suspended in a mixture of 10 ml of methanol and 25 ml of benzonitrile under nitrogen in a 100 ml round flask provided with gas inlet, stirrer, reflux condenser and fractionating column. The whole was thoroughly mixed and dimethylphosphine was introduced thereinto until a clear solution was obtained. The reaction temperature was at most 40° C. Following this, the reaction temperature was increased gradually to 130° C. The cooling liquid in the reflux condenser had a temperature of 65° – 70° C which made it possible for the alcohol to distil off. Once the desirable reaction temperature was reached, the reaction mixture was stirred for altogether a further 8 hours at 130° C. The solvent was removed by distillation under vacuum and 90.8 g of a slightly yellowish highly viscous residue, which crystallized gradually on cooling, was obtained. NMR-spectroscopy indicated that it contained 77.0% of trimethylphosphine oxide. The product could be further purified in known manner, e.g. by distillation or recrystallization.

EXAMPLE 10

The procedure was the same as that described in Example 9 save that 4.5 g of $BF_3$.etherate was added, once the desirable rearrangement temperature was reached. The reaction was complete after as short a period as 8.5 hours. This was easy to identify by titration with iodine in an acid medium. The crude trimethylphosphine oxide so obtained was worked up and purified in the manner described hereinabove.

We claim:
1. In the process for making tertiary methylphosphine oxides of the formula

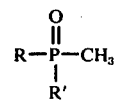

in which R and R' are identical or different alkyl groups other than a hydroxymethyl group, having from 1 to 6 carbon atoms by rearranging tertiary mono(hydroxymethyl)-phosphines of the formula

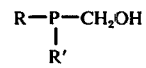

in which R and R' have the meanings given above, in the presence of a catalyst and in the absence of oxygen, water and alcohol at temperatures within the range minus 10° C and plus 250° C, the improvement which comprises using $BF_3$.etherate as catalyst.

2. The process as claimed in claim 1, wherein said alkyl groups have 1 or 2 carbon atoms.

3. The process as claimed in claim 1, wherein the rearrangement of the tertiary hydroxymethyl-phosphines is effected in a thin layer evaporator, tubular reactor or packed column.

4. The process as claimed in claim 1, wherein the rearrangement reaction is effected at temperatures within the range minus 10° and plus 180° C.

* * * * *